US011434183B2

(12) United States Patent
Su et al.

(10) Patent No.: US 11,434,183 B2
(45) Date of Patent: Sep. 6, 2022

(54) CATALYST FOR PREPARING ETHYLBENZENE FROM ETHANOL AND BENZENE, PREPARATION THEREFOR AND USE THEREOF

(71) Applicant: DALIAN INSTITUTE OF CHEMICAL PHYSICS, CHINESE ACADEMY OF SCIENCES, Dalian (CN)

(72) Inventors: Xiong Su, Dalian (CN); Xiaoli Yang, Dalian (CN); Yanqiang Huang, Dalian (CN); Tao Zhang, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

(21) Appl. No.: 17/262,677

(22) PCT Filed: Jul. 27, 2018

(86) PCT No.: PCT/CN2018/097323
§ 371 (c)(1),
(2) Date: Jan. 22, 2021

(87) PCT Pub. No.: WO2020/019276
PCT Pub. Date: Jan. 30, 2020

(65) Prior Publication Data
US 2021/0309590 A1 Oct. 7, 2021

(30) Foreign Application Priority Data

Jul. 23, 2018 (CN) .......................... 201810812858.6

(51) Int. Cl.
| | | |
|---|---|---|
| *C07C 2/86* | (2006.01) | |
| *B01J 29/70* | (2006.01) | |
| *B01J 35/02* | (2006.01) | |
| *B01J 35/10* | (2006.01) | |
| *B01J 37/00* | (2006.01) | |
| *B01J 37/04* | (2006.01) | |
| *B01J 37/06* | (2006.01) | |
| *B01J 37/08* | (2006.01) | |
| *B01J 37/10* | (2006.01) | |
| *C07C 15/073* | (2006.01) | |
| *B01J 29/04* | (2006.01) | |

(52) U.S. Cl.
CPC .............. *C07C 2/864* (2013.01); *B01J 29/70* (2013.01); *B01J 35/023* (2013.01); *B01J 35/1057* (2013.01); *B01J 35/1061* (2013.01); *B01J 37/0081* (2013.01); *B01J 37/04* (2013.01); *B01J 37/06* (2013.01); *B01J 37/082* (2013.01); *B01J 37/10* (2013.01); *C07C 15/073* (2013.01); *B01J 29/041* (2013.01); *C07C 2529/70* (2013.01)

(58) Field of Classification Search
CPC ... C07C 2/864; C07C 2529/70; C07C 15/073; Y02P 20/52; B01J 35/023; B01J 35/1057; B01J 35/1061; B01J 37/0081; B01J 37/04; B01J 37/06; B01J 37/082; B01J 37/0018; B01J 37/10; B01J 29/041
USPC ................................ 585/446, 447, 467, 469
See application file for complete search history.

(56) References Cited

U.S. PATENT DOCUMENTS

| | | |
|---|---|---|
| 3,751,504 A | 8/1973 | Keown et al. |
| 3,751,506 A | 8/1973 | Burress et al. |
| 4,016,218 A | 4/1977 | Haag et al. |
| 4,547,605 A | 10/1985 | Kresge et al. |
| 4,891,458 A | 1/1990 | Innes et al. |
| 5,227,558 A | 7/1993 | Shamshoum et al. |
| 10,967,350 B2 | 4/2021 | Zhang et al. |
| 11,179,714 B2 | 11/2021 | Liu et al. |
| 11,311,852 B2 | 4/2022 | Zhang et al. |
| 2021/0403332 A1 | 12/2021 | Yuan et al. |
| 2021/0403333 A1 | 12/2021 | Yuan et al. |
| 2022/0002481 A1 | 1/2022 | Yuan et al. |
| 2022/0002496 A1 | 1/2022 | Xing et al. |
| 2022/0008902 A1 | 1/2022 | Yuan et al. |

FOREIGN PATENT DOCUMENTS

| | | |
|---|---|---|
| CN | 1506340 A | 6/2004 |
| CN | 1194944 C | 3/2005 |
| CN | 101664695 A | 3/2010 |
| CN | 102040459 A | 5/2011 |

(Continued)

OTHER PUBLICATIONS

Hong et al., "Synthesis, Crystal Structure, Characterization, and Catalytic Properties of TNU-9", J. Am. Chem. Soc., 2007, 129, pp. 10870-10885.*

(Continued)

*Primary Examiner* — Elizabeth D Wood
(74) *Attorney, Agent, or Firm* — Seed IP Law Group LLP (57) ABSTRACT

Disclosed is a catalyst for producing ethylbenzene in one-step by vapor phase alkylation reaction of ethanol and benzene. The catalyst has the following features for the reaction: high alkylation reaction activity, high selectivity of ethylbenzene in an alkylation product, high hydrothermal stability and stable catalytic performance. The catalyst comprises a mesoporous-microporous composite TNU-9 molecular sieve and the silicon to aluminum molar ratio, $SiO_2/Al_2O_3$, of the meso-microporous composite TNU-9 molecular sieve ranges from 50 to 200.

17 Claims, 3 Drawing Sheets

(56) References Cited

FOREIGN PATENT DOCUMENTS

| | | |
|---|---|---|
| CN | 102274746 A | 12/2011 |
| CN | 102276413 A | 12/2011 |
| CN | 102872899 A | 1/2013 |
| CN | 102875315 A | 1/2013 |
| CN | 103121909 A | 5/2013 |
| CN | 105597814 A | 5/2016 |
| CN | 105665004 A | 6/2016 |
| CN | 107552087 A | 1/2018 |
| KR | 2003-0082022 A | 10/2003 |
| WO | 2010/143043 A1 | 12/2010 |
| WO | 2011/077240 A1 | 6/2011 |
| WO | 2016/099408 A1 | 6/2016 |

OTHER PUBLICATIONS

Hu., et al., "Effect of mesopore structure of TNU-9 on methane dehydroaromatization", RSC Advances, 4(51), 2014, pp. 26577-26584.*

"Synthesis, characterization and catalytic application of hierarchical porous IM-5 and TNU-9 zeolites," Chinese Doctoral Dissertations Full-text Database, Engineering Science and Technology, URL= http://www.cdfd.cnki.net/Journal/Issue.aspx?dbCode=CDFD&PYKM=BBBD&Year=2014&Issue=09&Volume=01&QueryID=26, accessed May 10, 2020, 23 pages, (with English abstract).

International Search Report, dated Apr. 22, 2019, for International Application No. PCT/CN2018/097323, 5 pages.

Odedairo et al., "Ethylation of benzene: Effect of zeolite acidity and structure," *Applied Catalysis A: General* 355:31-45, 2010.

Extended European Search Report, dated Mar. 29, 2022, for European Application No. 18927322,0-1104, 8 pages.

Heng, "Chapter V: Synthesis, Characterization, and Catalytic Applications of Multilevel Poromolybdenyl TNU-9 Molecular Sieves SA Introduction," *Synthesis of the fifth jujube multilevel pore TNU-9 molecule, table slave and catalytic function*:77-84 (10 pages).

Hong et al., "Synthesis, Structure Solution, Characterization, and Catalytic Properties of TNU-10: A High-Silica Zeolite with the STI Topology," *J. Am. Chem. Soc.* 126(18):5817-5826, Apr. 2004 (11 pages).

Portilla et al., "Structure-reactivity relationship for aromatics transalkylation and isomerization process with TNU-9, MCM-22 and ZSM-5 zeolites, and their industrial implications," *Applied Catalysis A: General* 393:257-268, 2011.

* cited by examiner

Topology of [010] face

CATALYST FOR PREPARING ETHYLBENZENE FROM ETHANOL AND BENZENE, PREPARATION THEREFOR AND USE THEREOF

FIELD

The present invention relates to a catalyst for producing ethylbenzene from ethanol and benzene, preparation method and use thereof.

BACKGROUND

Ethylbenzene is an important and basic organic raw material in industry, mainly used for catalytic dehydrogenation to produce styrene which is further used in the field of polymer materials to produce rubber and plastics. The ethylbenzene can also be used as a solvent or diluent and be used to produce diethylbenzene. With the rapid development of social economy, the market demand and production capacity of ethylbenzene are showing an obvious upward trend. Statistics show that, from 1998 to 2015, the global demand for ethylbenzene increased by 3.7% annually, and our country's annual growth rate reached 5.3%, from 800 kt in 1998 to 2 Mt in 2015.

At present, the industrial production of ethylbenzene is mainly through the alkylation reaction of benzene and ethylene. The main processes include $AlCl_3$ liquid-phase alkylation and molecular sieve alkylation. The $AlCl_3$ liquid-phase alkylation has advantages of simple process, mild operating conditions, and high ethylene conversion rate, but it has problems such as equipment corrosion, environmental pollution, and high maintenance costs. The molecular sieve alkylation mainly includes the ZSM-5 molecular sieve vapor-phase alkylation (see U.S. Pat. Nos. 3,751,504, 3,751,506, 4,016,218 and 4,547,605) developed by Mobil and Badger companies to produce ethylbenzene, and the Beta molecular sieve and Y-type molecular sieve liquid-phase alkylation (see, U.S. Pat. Nos. 4,891,458, 5,227,558 and ZL02151177) developed by UOP and Lummus companies. These methods have the advantages of no corrosion, no pollution, simple process, high heat recovery and utilization rate and the like. With the depletion of petroleum resources and the soaring price of petroleum, the cost of ethylene alkylation has increased significantly, and thus it has become a trend to seek new raw materials for replacing ethylene to produce ethylbenzene. With the continuous progress and maturity of coal-based ethanol and bio-ethanol technologies in recent years, the price and production costs of ethanol have shown a downward trend, making its application prospects more promising. The use of environmentally friendly renewable ethanol as the alkylation reagent can significantly reduce the production cost of ethylbenzene, and improve the economic efficiency and comprehensive competitiveness of the enterprise, thereby making the process more attractive and have a higher society value.

The process for producing ethylbenzene from ethanol refers to the simultaneous occurrence of ethanol dehydration reaction and the alkylation reaction of ethylene and benzene in a reactor containing ethanol and benzene. The catalyst used therefore not only needs to meet high conversion rate of ethanol and dehydration selectivity, but also has certain requirements for the catalytic efficiency of the alkylation between ethylene and benzene. China Petroleum & Chemical Corporation obtained a series of catalysts based on ZSM-5 by adding binder and modifying the ZSM-5 with rare earth oxides or alkaline earth metal oxides. The treated catalyst was used in the ethylbenzene production reaction. It was found that under the conditions with a temperature of 390° C., a pressure of 1.2 MPa, ethanol weight hourly space velocity of 0.8 $h^{-1}$ and a molar ratio between benzene and ethanol of 6.5, the selectivity of ethylbenzene can be as high as 99%. The period for needing regeneration of the treated catalyst is half a year (see, CN103121909A, CN102872899A, CN102276413A, CN 102875315 and CN102274746A). Zheng Xinyuan et al. used β molecular sieve as a catalyst and obtained the ethanol conversion rate with greater than 99% and the ethylbenzene yield with greater than 80% under the condition that a temperature was in a range from 240 to 260° C., n(benzene):n(ethylene) was in a range from 4 to 6 and a space velocity of benzene was in a range from 3 to 5 $h^{-1}$ (see, Chemical Reaction Engineering and Technology, 2006, 22, 172-175). Similarly, Versalis, Italy, used a zeolite with BEA structure as a catalyst to catalyze the alkylation reaction of bioethanol and benzene (see, WO2011077240). WO2010143043 proposed the use of MTW family zeolite as a catalyst to catalyze the alkylation reaction of benzene and ethanol obtained by fermenting biomass-derived sugar as an alkylating agent to produce ethylbenzene, which greatly improved the economy of the reaction. In addition to the above-mentioned molecular sieve catalysts, Ehsan Rahmani et al. recently used MOF materials, such as Fe-based MIL-110 and Al—Li doped MIL-53, to catalyze the reaction of benzene and ethanol to produce ethylbenzene, under relatively mild reaction conditions (i.e., a temperature in a range from 175 to 200° C.). As a result, a selectivity of ethylbenzene was greater than 75% (see, Microporous and Mesoporous Materials, 2017, 249, 118-127; Ind. Eng. Chem. Res. 2018, 57, 169-178). This research provides a new solution for the selection of reaction catalysts and the control of reaction conditions, but there is still a long way to go before industrialization. Thus, molecular sieve catalysts are still key at present.

In view of the various molecular sieves in the market, the researchers compared their catalytic performance for the reaction of benzene and ethanol. Sun Linping et al. investigated the catalytic performance of ZSM-5, Beta and Y zeolite in the vapor-phase alkylation reaction of coked benzene and ethanol. The results showed that the cage structure in the channels of Beta and Y zeolite easily generates macromolecules, which leads to rapid deactivation of the catalyst, while ZSM-5 molecular sieve showed good resistance to deactivation, see, Acta Petrolei Sinica (Petroleum Processing), 2006, 22, 146-148. Odedairo et al. compared the catalytic reaction performance of MOR and ZSM-5 molecular sieves, and concluded that the selectivity of ethylbenzene over ZSM-5 is higher (see, Catalysis Today, 2013, 204, 73-84). Gao Junhua et al., State Key Laboratory of Coal Conversion, Shanxi Institute of Coal Chemistry, Chinese Academy of Sciences, compared the catalytic performance of molecular sieves with different structures in the vapor-phase alkylation of benzene and ethanol to produce ethylbenzene and reached a similar conclusion. The catalytic performance of ZSM-5 molecular sieve was more ideal, the activity thereof was higher and the stability was good. However, if the channel diameter of the ZSM-5 catalyst is too small, the mass transfer of the reaction is easily affected, causing the occurrence of side reactions which in turn results in coking and deactivation of the catalyst. Further, the ZSM-5 catalyst has poor hydrothermal stability, and thus the structure thereof is easy to collapse and the catalyst is easy to deactivate during the reaction. Document Applied Catalysis A: General, 2010, 385, 31-45 compared catalytic performance in alkylation by ethanol of two molecular sieves, i.e., SSZ-33 and TNU-9 molecular sieves, which have similar channel structure to ZSM-5. The alkylation by ethanol was performed under the condition that a ratio of benzene to ethanol was 1:1, and the temperature was in a range from 250 to 300° C. The conversion rate of ethanol over TNU-9 molecular sieve was higher than that over ZSM-5, but the selectivity of ethylbenzene over TNU-9 molecular sieve was low. However, the document lacks detailed descriptions on the synthesis and physicochemical properties of TNU-9 molecular sieve and the conditions for the vapor-phase alkylation of benzene and ethanol are relatively narrow.

SUMMARY

The present invention relates to a catalyst with high activity and high stability for the vapor-phase alkylation of ethanol and benzene to produce ethylbenzene and a preparation method thereof. Specifically, the catalyst used in the present invention is TNU-9 molecular sieve with a composite structure comprising mesopores and micropores. The present invention is mainly aimed to achieve the hydrothermal stability, high alkylation activity and high selectivity of ethylbenzene of the catalyst by synthesizing the mesoporous-microporous composite TNU-9 molecular sieve with high silicon content. The detailed preparation method of the catalyst is as follow: mesoporous silica, MCM-48 or SBA-15 as silicon source, and 1,4-MPB as template are used to synthesize TNU-9 molecular sieve by hydrothermal synthesis. The obtained catalyst is used in the alkylation reaction of ethanol and benzene, wherein the reaction temperature ranges from 300 to 500° C., the reaction pressure ranges from 0.1 to 2 MPa, the weight hourly space velocity of the feed ranges from 3 to 8 $h^{-1}$, the ratio of benzene to ethanol ranges from 3 to 7, and the main products are ethylbenzene and water. The catalyst of the present invention can be used stably for a long time in the vapor-phase alkylation of ethanol and benzene to directly produce ethylbenzene, and can maintain good catalytic performance of the alkylation reaction of benzene and ethanol. The three-dimensional TNU-9 molecular sieve obtained by hydrothermal synthesis in the present invention, which comprises a 10-ring structure with intersected porous channels and a mesoporous-microporous composite structure, is used in vapor-phase alkylation reaction of ethanol and benzene to produce ethylbenzene in one-step. The catalyst not only has high alkylation activity and high selectivity of ethylbenzene, but also has certain hydrothermal stability and stable catalytic performance. The present invention provides a new catalyst for the reaction of ethanol and benzene to produce ethylbenzene, which has a good application prospect.

According to one aspect of the present application, there is provided a catalyst for vapor-phase alkylation of ethanol and benzene to produce ethylbenzene in one-step. This catalyst performs a high alkylation activity, achieves high selectivity of ethylbenzene in the product of the alkylation, and also has high hydrothermal stability and stable catalytic performance.

The molecular sieve catalyst comprises mesoporous-microporous composite TNU-9 molecular sieve, wherein, the silicon to aluminum molar ratio, i.e., $SiO_2/Al_2O_3$, of the TNU-9 molecular sieve ranges from 50 to 200.

Optionally, the upper limit of the silicon to aluminum molar ratio, $SiO_2/Al_2O_3$ of the mesoporous-microporous composite TNU-9 molecular sieve is 200, 190, 180, 170, 160, 150, 140, 130, 120, 110 or 100; and the lower limit thereof is 100, 95, 90, 85, 80, 75, 72, 70, 68, 65, 64, 63, 60, 58, 56, 55, 52 or 50.

Optionally, the silicon to aluminum molar ratio, $SiO_2/Al_2O_3$, of the mesoporous-microporous composite TNU-9 molecular sieve ranges from 50 to 100.

Optionally, the silicon to aluminum molar ratio, $SiO_2/Al_2O_3$, of the mesoporous-microporous composite TNU-9 molecular sieve ranges from 60 to 100.

Optionally, the silicon to aluminum molar ratio, $SiO_2/Al_2O_3$, of the mesoporous-microporous composite TNU-9 molecular sieve ranges from 60 to 80.

Optionally, the mesoporous-microporous composite TNU-9 molecular sieve comprises a structure of micropore channel and mesopore channel, and the diameter of the mesopore channel ranges from 3 to 50 nm.

Optionally, the mesoporous-microporous composite TNU-9 molecular sieve is in a form of crystal grain accumulation, and the diameter of a single crystal grain ranges from 100 to 1000 nm.

Optionally, the mesoporous-microporous composite TNU-9 molecular sieve comprises micropores with a pore diameter ranging from 0.3 to 0.8 nm.

Optionally, the mesoporous-microporous composite TNU-9 molecular sieve comprises micropores with a pore diameter ranging from 0.4 to 0.7 nm.

Optionally, the mesoporous-microporous composite TNU-9 molecular sieve comprises mesopores with a pore diameter ranging from 6 to 13 nm.

Optionally, the upper limit of the pore diameter of the mesopores included in the mesoporous-microporous composite TNU-9 molecular sieve is 13 nm, 12 nm, 11 nm or 10 nm and the lower limit thereof is 9 nm, 8 nm, 7 nm or 6 nm.

Specifically, the catalyst is mesoporous-microporous composite TNU-9 molecular sieve with high silicon content, wherein the diameter of mesopore channel of the molecular sieve ranges from 3 to 50 nm, and the silicon to aluminum molar ratio, $SiO_2/Al_2O_3$, of the molecular sieve ranges from 50 to 200. The catalyst is in a form of small crystal grain accumulation, with a single crystal grain diameter in a range from 100 to 1000 nm.

Optionally, the molecular sieve is used to catalyze the reaction of ethanol and benzene to produce ethylbenzene.

According to another aspect of the present application, there is provided a preparation method of a catalyst for vapor-phase alkylation by ethanol to produce ethylbenzene in one-step, which is simple and reliable and is convenient for industrial production.

The preparation method of the catalyst comprises the following steps:

(1) adding an aluminum source, an alkali source, and a silicon source comprising mesopore structure to an aqueous solution containing a template and then stirring to obtain a gel-like precursor;

(2) crystallizing hydrothermally the gel-like precursor obtained in step (1);

(3) washing the product obtained in step (2) to be neutral and drying the product; and (4) calcining the product obtained in step (3) to obtain the molecular sieve catalyst.

Optionally, a molar ratio of the aluminum source, alkali source, silicon source comprising mesopore structure, and template in step (1) satisfies: $SiO_2:Al_2O_3:M_2O:R:H_2O=(5\sim100):1:(1\sim30):(5\sim20):(1000\sim4000)$;

wherein, R represents the template and is calculated by the molar number of the template itself, the molar number of the aluminum source is calculated by the molar number of $Al_2O_3$, the molar number of the alkali source is calculated by the molar number of its corresponding alkali metal oxide $M_2O$, the molar number of silicon source is calculated by the molar number of $SiO_2$, and the molar number of water is calculated by the molar number of $H_2O$ itself.

Optionally, the template in step (1) comprises at least one of 1,4-MPB, glucose and activated carbon.

Optionally, the method for preparing 1,4-MPB comprises: subjecting a solution comprising 1,4-dibromobutane and N-methyltetrahydropyrrole to refluxing, recrystallizing and drying to obtain 1,4-MPB.

Optionally, the solution comprising 1,4-dibromobutane and N-methyltetrahydropyrrole is obtained by placing 1,4-dibromobutane and N-methyltetrahydropyrrole in acetone;
the refluxing is performed at a temperature ranging from 30 to 80° C. in water bath;
a step of extraction by acetone occurs before the recrystallization;
a solvent for recrystallization includes a mixed solvent of methanol and diethyl ether; wherein the volume ratio of methanol and diethyl ether is (0.05~50):(1~20);
the drying is performed at a temperature ranging from 60 to 120° C. for a time ranging from 5 to 20 h.

Optionally, the refluxing is performed in water bath for a time ranging from 6 to 48 h.

Optionally, the silicon source comprising mesopore structure in step (1) is at least one of silica comprising mesopore structure, MCM-48, and SBA-15.

Optionally, the aluminum source in step (1) is at least one of sodium metaaluminate, aluminum powder, aluminum nitrate and aluminum hydroxide, and the alkali source is at least one of sodium hydroxide and potassium hydroxide.

Optionally, the stirring in step (1) is performed for a time ranging from 5 to 24 hours.

Optionally, the hydrothermal crystallization in step (2) refers to hydrothermal dynamic crystallization; and the hydrothermal dynamic crystallization is performed at a temperature ranging from 120 to 260° C. for a time ranging from 100 to 360 hours.

Optionally, the upper limit of the temperature for crystallization is 260° C., 240° C., 220° C., 200° C., 180° C., 160° C., or 140° C., and the lower limit thereof is 140° C., 130° C., or 120° C.

Optionally, the upper limit of the time for crystallization is 360 h, 340 h, 300 h or 280 h, and the lower limit thereof is 280 h, 260 h, 240 h, 200 h, 180 h, 160 h, 140 h, 120 h or 100 h.

Optionally, the dynamic crystallization in step (2) is rotational crystallization, and the rotation speed ranges from 5 to 30 rpm.

Optionally, the upper limit of the rotation speed is 30 rpm, 25 rpm, 20 rpm, or 15 rpm, and the lower limit thereof is 15 rpm, 10 rpm or 5 rpm.

Optionally, the temperature for calcining in step (4) ranges from 200 to 600° C., and the time for calcining ranges from 1 to 20 h.

Optionally, the upper limit of the temperature for calcining is 600° C., 580° C., 550° C., 520° C., 500° C. or 450° C., and the lower limit thereof is 450° C., 400° C., 300° C. or 200° C.

Optionally, the upper limit of the time for calcining is 20 h, 18 h, 15h, 12 h, or 10 h, and the lower limit thereof is 10 h, 8 h, 5 h, 3 h, or 1 h.

Optionally, step (3) comprises filtering and washing the product obtained in step (2) until the washing liquid is neutral, and then drying the product at a temperature ranging from 60 to 110° C.

As an embodiment, the method comprises the following steps:
1. Synthesis of 1,4-MPB template
dissolving 1,4-dibromobutane and N-methyltetrahydropyrrole in acetone, heating them to a temperature ranging from 30 to 80° C., refluxing for a time ranging from 6 to 48 h; extracting the obtained reaction solution by acetone, and recrystallizing the obtained product by a mixed solvent of methanol and diethyl ether; drying the recrystallized product in a vacuum drying oven at a temperature ranging from 60 to 120° C. for a time ranging from 5 to 20 h to obtain the template R;
2. Preparation of TNU-9 molecular sieve
dissolving the template R obtained in step 1) in water, and then adding sequentially an aluminum source, an alkali source and a silicon source comprising mesopore structure to obtain a solution I, wherein a molar ratio of raw materials in the solution I was $SiO_2:Al_2O_3:M_2O:R:H_2O$=(5~100):1:(1~30):(5~20):(1000~4000); after stirring for a time ranging from 5 to 24 hours, the solution I will form a gel; putting the gel into a reactor, and performing crystallization for a time ranging from 100 to 360 h under the dynamic and hydrothermal conditions driven by a motor at a temperature ranging from 120 to 260° C.; filtering and washing the obtained product until the washing liquid is neutral, and drying the filter cake at a temperature ranging from 60 to 110° C.; calcining the dried filter cake in a muffle furnace at a temperature ranging from 200 to 600° C. for a time ranging from 1 to 20 h to obtain the molecular sieve catalyst.

As an embodiment, the method comprises the following steps:
1. Synthesis of 1,4-MPB template
putting 1,4-dibromobutane and N-methyltetrahydropyrrole in acetone and subjecting them to refluxing in a water bath with a temperature ranging from 30 to 80° C.; extracting excess amine by acetone, and placing the resulting mixture in a mixed solvent of methanol and diethyl ether to perform recrystallization; transferring the recrystallized product to a vacuum drying oven at a temperature ranging from 60 to 120° C. for a time ranging from 5 to 20 h to obtain the template;
2. Preparation of TNU-9 molecular sieve
dissolving the template obtained in step 1 in water, and then adding sequentially an aluminum source, an alkali source and a silicon source comprising mesopore structure therein, wherein all raw materials are respectively calculated according to molar number of $SiO_2$, $Al_2O_3$, $M_2O$, R, $H_2O$, and the molar ratio thereof is $SiO_2:Al_2O_3:M_2O:R:H_2O$=(5~100):1:(1-30):(5-20):(1000~4000), wherein R represents the template in step 1 and M represents the alkali metal; stirring the obtained solution vigorously for a time ranging from 5 to 24 h to form a gel, which is then placed into a stainless steel reactor; performing crystallization under the dynamic and hydrothermal conditions driven by a motor for a time ranging from 100 to 360 h and at a temperature ranging from 120 to 260° C.; filtering and washing the obtained product until the washing liquid is neutral, and transferring the filter cake to an oven at a temperature ranging from 60 to 110° C. for drying; placing the dried filter cake in a muffle furnace and calcining the dried filter cake at a temperature ranging from 200 to 600° C. for a time ranging from 1 to 20 h to obtain the TNU-9 molecular sieve with a composite structure comprising mesopores and micropores.

In step 1, the refluxing is performed for a time ranging from 6 to 48 hours.

In step 2, the aluminum source is at least one of sodium metaaluminate, aluminum powder, aluminum nitrate, and aluminum hydroxide; and the alkali source is at least one of sodium hydroxide and potassium hydroxide; the silicon source used in step 2 is at least one of silica comprising mesopore structure, MCM-48 and SBA-15; the crystallization in step 2 refers to the rotational crystallization driven by a motor, and the rotation speed thereof ranges from 5 to 30 rpm;

The catalyst is used for the reaction of producing ethylbenzene from ethanol. The reaction conditions are as follow: the catalyst is loaded in a reaction tube of a fixed bed reactor for evaluating the catalytic performance of the catalyst, the raw materials are benzene and ethanol, the molar ratio of benzene to ethanol ranges from 3:1 to 7:1, the weight hourly space velocity of the raw materials ranges from 3 to 8 $h^{-1}$, the reaction temperature ranges from 300 to 500° C., and the reaction pressure ranges from 0.1 to 2 MPa.

According to another aspect of the present disclosure, there is provided the use of the above molecular sieve catalyst, and/or the molecular sieve catalyst obtained by the preparation method described above in the production of ethylbenzene by vapor phase alkylation reaction of ethanol and benzene.

According to another aspect of the present application, there is provided a method for producing ethylbenzene by vapor-phase alkylation of ethanol and benzene, wherein the method comprises the following steps:

feeding the raw materials comprising benzene and ethanol to a fixed bed reactor loaded with catalyst to react to obtain ethylbenzene;

wherein, the catalyst comprises at least one of the above molecular sieve catalyst and the molecular sieve catalyst prepared by the above method.

Optionally, the reaction temperature ranges from 300 to 500° C., the reaction pressure ranges from 0.1 to 2 MPa, the molar ratio of benzene to ethanol in the raw material ranges from 3:1 to 7:1, and the weight hourly space velocity of the raw materials ranges from 3 to 8 $h^{-1}$.

The catalyst comprises at least one of the above molecular sieve catalyst and the molecular sieve catalyst prepared by the above preparation method.

Optionally, under the reaction conditions that the molar ration of benzene to ethanol ranges from 4:1 to 7:1, the reaction temperature ranges from 350 to 470° C., and the weight hourly space velocity of the raw materials ranges from 4 to 8 $h^{-1}$, the selectivity of ethylbenzene is greater than 93%.

In this application, "MCM-48 molecular sieve" belongs to the M41S series of mesoporous molecular sieves, which comprise a uniform pore diameter of about 2.6 nm and two sets of mutually independent three-dimensionally spiral porous channel network structures.

"SBA-15 molecular sieve" is mesoporous molecular sieve belonging to the P3 mm space group, which comprises mesopores with a two-dimensional hexagonal through-hole structure.

1,4-MPB refers to the abbreviation for 1,4-bis(N-methylpyrrole)butane.

The present application achieves the following beneficial effects:

1) The preparation method of the catalyst provided by this application is reliable, simple and has stable repeatability;

2) The catalyst provided in this application can effectively convert ethanol into ethylbenzene in one step, simplifying the process, saving equipment investment, and reducing production costs;

3) The catalyst provided by this application is applied to the process of producing ethylbenzene by the vapor-phase alkylation reaction of ethanol and benzene. Compared with the prior art, the catalyst herein has improved hydrothermal stability and achieves higher selectivity of ethylbenzene in the product. The catalytic evaluation results show that, under the reaction conditions that the molar ratio of benzene to ethanol ranges from 4:1 to 7:1, the reaction temperature ranges from 350 to 470° C. and the weight hourly space velocity of raw materials ranges from 4 to 8 $h^{-1}$, the selectivity of ethylbenzene is greater than 93%;

4) The catalyst provided by this application has high hydrothermal stability and catalytic reaction stability. After the molecular sieve is calcined at 650° C., the relative crystallinity decreases by about 15%; under the condition that the molecular sieve is subject to saturated water steam treatment at 800° C., the relative crystallinity decreases only about 30%. The catalyst has good application prospects and high application value.

DETAILED DESCRIPTION

The present application will be described in detail below with reference to the examples, but is not limited to these examples.

Unless otherwise specified, the raw materials in the examples of the present application are all commercially available.

The silica containing mesopore structure was purchased from Nankai University Molecular Sieve Co., Ltd., and its diameter of mesopores was 15 nm.

MCM-48 molecular sieve was purchased from Nankai University Molecular Sieve Co., Ltd., and its silicon to aluminum ratio was 30.

SBA-15 molecular sieve was purchased from Nankai University Molecular Sieve Co., Ltd., and its silicon to aluminum ratio was 40.

The analysis methods used in the examples in the present application are as follows: X'pert-Pro X-ray diffractometer manufactured by PANAnalytical Company in the Netherlands was used for XRD pattern analysis.

HITACHI S-5500 FE-SEM electron microscope was used for SEM morphological analysis.

PANAlytical Epsilon 5 Energy dispersive X-ray Fluorescence Spectrometer ED-XRF was used to test the ratio of silicon to aluminum.

ASAP-2010 Physical Adsorption Instrument from Micromeritics was used to test pore structure.

In the examples of the present application, the conversion of ethanol and benzene, and selectivity of ethylbenzene are all calculated based on the molar number of carbon.

Example 1

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 150 mL water, and then 0.14 g aluminum powder, 3.6 g sodium hydroxide and 20 g mesoporous silica were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 60, the diameter of micropores was 0.55 nm and the diameter of mesopores was 6 nm.

Example 2

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 150 mL water, and then 0.14 g aluminum powder, 3.6 g sodium hydroxide and 15 g MCM-48 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 50, the diameter of micropores was 0.55 nm and the diameter of mesopores was 6 nm.

Example 3

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 150 mL water, and then 0.14 g aluminum powder, 3.6 g sodium hydroxide and 15 g SBA-15 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 56, the diameter of micropores was 0.55 nm and the diameter of mesopores was 6 nm.

Example 4

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 12 h to obtain the 1,4-MPB template. 10.7 g 1,4-MPB template was dissolved in 150 mL water, and then 0.14 g aluminum powder, 3.6 g sodium hydroxide and 30 g mesoporous silica were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 75, the diameter of micropores was 0.55 nm and the diameter of mesopores was 6 nm.

Example 5

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 12 h to obtain the 1,4-MPB template. 15.8 g 1,4-MPB template was dissolved in 150 mL water, and then 0.14 g aluminum powder, 3.6 g sodium hydroxide and 20 g mesoporous silica were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 60, the diameter of micropores was 0.55 nm and the diameter of mesopores was 10 nm.

Example 6

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 12 h to obtain the 1,4-MPB template. 21.5 g 1,4-MPB template was dissolved in 150 mL water, and then 0.14 g aluminum powder, 3.6 g sodium hydroxide and 20 g mesoporous silica were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 60, the diameter of micropores was 0.55 nm and the diameter of mesopores was 13 nm.

Example 7

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 150 mL water, and then 2.0 g aluminum nitrate nonahydrate, 3.6 g sodium hydroxide and 15 g MCM-48 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 50, the diameter of micropores was 0.55 nm and the diameter of mesopores was 6 nm.

Example 8

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 12 h to obtain the 1,4-MPB template. 10.7 g 1,4-MPB template was dissolved in 150 mL water, and then 0.14 g aluminum powder, 3.6 g sodium hydroxide and 15 g MCM-48 molecular sieve were added therein sequentially. The resulting solution was stirred for 10 h to form a gel-like mixture. The gel-like mixture was then put into a 200 mL stainless steel reactor, and was subject to rotational hydrothermal crystallization at 180° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 63, the diameter of micropores was 0.55 nm and the diameter of mesopores was 6 nm.

Example 9

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 12 h to obtain the 1,4-MPB template. 10.7 g 1,4-MPB template was dissolved in 150 mL water, and then 0.14 g aluminum powder, 3.6 g sodium hydroxide and 15 g MCM-48 molecular sieve were added therein sequentially. The resulting solution was stirred for 10 h to form a gel-like mixture. The gel-like mixture was then put into a 200 mL stainless steel reactor, and was subject to rotational hydrothermal crystallization at 200° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 65, the diameter of micropores was 0.55 nm and the diameter of mesopores was 6 nm.

Example 10

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 8 h to obtain the 1,4-MPB template. 10.7 g 1,4-MPB template was dissolved in 150 mL water, and then 0.14 g aluminum powder, 3.6 g sodium hydroxide and 15 g MCM-48 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 360 h and at a rotation speed of 10 rpm. The resulting product was filtered and washed until the washing liquid was neutral, and the filter cake was transferred to an oven at 80° C. to perform drying for 12 h. Then the resulting sample was calcined in a muffle furnace at 500° C. for 6 h to obtain TNU-9 molecular sieve. The silicon to aluminum ratio of the TNU-9 molecular sieve was 58, the diameter of micropores was 0.55 nm and the diameter of mesopores was 6 nm.

Example 11

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 15 h to obtain the 1,4-MPB template. 10.7 g 1,4-MPB template was dissolved in 150 mL water, and then 0.14 g aluminum powder, 3.6 g sodium hydroxide and 15 g MCM-48 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 20 rpm. The resulting product was filtered and washed until the washing liquid was neutral, and the filter cake was transferred to an oven at 80° C. to perform drying for 12 h. Then the resulting sample was calcined in a muffle furnace at 500° C. for 6 h to obtain TNU-9 molecular sieve. The silicon to aluminum ratio of the TNU-9 molecular sieve was 52, the diameter of micropores was 0.55 nm and the diameter of mesopores was 7 nm.

Example 12

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 8 h to obtain the 1,4-MPB template. 10.7 g 1,4-MPB template was dissolved in 150 mL water, and then 2.0 g aluminum nitrate nonahydrate, 3.6 g sodium hydroxide and 15 g SBA-15 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 240 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 500° C. for 6 h to obtain TNU-9 molecular sieve. The silicon to aluminum ratio of the TNU-9 molecular sieve was 56, the diameter of micropores was 0.55 nm and the diameter of mesopores was 10 nm.

Example 13

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 150 mL water, and then 1.5 g aluminum powder, 4.2 g potassium hydroxide and 20 g SBA-15 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 200 h and at a rotation speed of 15 rpm. The resulting product was filtered and washed until the washing liquid was neutral, and the filter cake was transferred to an oven at 80° C. to perform drying for 12 h. Then the resulting sample was calcined in a muffle furnace at 500° C. for 6 h to obtain TNU-9 molecular sieve. The silicon to aluminum ratio of the TNU-9 molecular sieve was 64, the diameter of micropores was 0.55 nm and the diameter of mesopores was 9 nm.

Example 14

21.6 g 1,4-dibromobutane and 17.2 g N-methyltetrahydropyrrole were placed in 100 mL acetone. The obtained solution was subject to refluxing in water bath at 70° C. for 20 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 75 mL water, and then 2.0 g sodium metaaluminate, 4.2 g potassium hydroxide and 20 g SBA-15 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 200 h and at a rotation speed of 30 rpm. The resulting product was filtered and washed until the washing liquid was neutral, and the filter cake was transferred to an oven at 80° C. to perform drying for 12 h. Then the resulting sample was calcined in a muffle furnace at 500° C. for 6 h to obtain TNU-9 molecular sieve. The silicon to aluminum ratio of the TNU-9 molecular sieve was 70, the diameter of micropores was 0.55 nm and the diameter of mesopores was 8 nm.

Example 15

21.6 g 1,4-dibromobutane and 17.2 g N-methyltetrahydropyrrole were placed in 100 mL acetone. The obtained solution was subject to refluxing in water bath at 70° C. for 20 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for 10 h to obtain the 1,4-MPB template. 10.7 g 1,4-MPB template was dissolved in 150 mL water, and then 2.0 g aluminum nitrate nonahydrate, 3.6 g sodium hydroxide and 24 g SBA-15 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C.

for 210 h and at a rotation speed of 10 rpm. The resulting product was filtered and washed until the washing liquid was neutral, and the filter cake was transferred to an oven at 80° C. to perform drying for 12 h. Then the obtained sample was calcined in a muffle furnace at 550° C. for 5 h to obtain TNU-9 molecular sieve. The silicon to aluminum ratio of the TNU-9 molecular sieve was 68, the diameter of micropores was 0.55 nm and the diameter of mesopores was 10 nm.

Example 16

21.6 g 1,4-dibromobutane and 17.2 g N-methyltetrahydropyrrole were placed in 100 mL acetone. The obtained solution was subject to refluxing in water bath at 60° C. for 24 h. The excess amine was extracted by acetone, and the resulting mixture was placed in 100 mL mixed solvent of methanol and diethyl ether (the volume ratio thereof was 2:1) to perform recrystallization. The resulting sample was transferred to a vacuum drying oven at a temperature of 80° C. to perform drying for a time ranging from 5 to 20 h to obtain the 1,4-MPB template. 10.7 g 1,4-MPB template was dissolved in 150 mL water, and then 1.6 g sodium metaaluminate, 3.6 g sodium hydroxide and 12 g SBA-15 molecular sieve were added therein sequentially. The resulting solution was stirred for 10 h to form a gel-like mixture. The gel-like mixture was then put into a 200 mL stainless steel reactor, and was subject to rotational hydrothermal crystallization at 160° C. for 300 h and at a rotation speed of 5 rpm. The resulting product was filtered and washed until the washing liquid was neutral, and the filter cake was transferred to an oven at 80° C. to perform drying for 12 h. Then the obtained sample was calcined in a muffle furnace at 550° C. for 5 h to obtain TNU-9 molecular sieve. The silicon to aluminum ratio of the TNU-9 molecular sieve was 72, the diameter of micropores was 0.55 nm and the diameter of mesopores was 12 nm.

Example 17

The procedures were the same as those in Example 1 except that the resulting solution was vigorously stirred for 5 h to form a gel-like mixture which was then put into a 200 ml stainless steel reactor.

Example 18

The procedures were the same as those in Example 1 except that the resulting solution was vigorously stirred for 24 h to form a gel-like mixture which was then put into a 200 ml stainless steel reactor.

Example 19

The procedures were the same as those in Example 1 except that the rotational hydrothermal crystallization was carried out at 120° C.

Example 20

The procedures were the same as those in Example 1 except that the rotational hydrothermal crystallization was carried out at 260° C.

Example 21

The procedures were the same as those in Example 1 except that the rotational hydrothermal crystallization was carried out for 100h.

Example 22

The procedures were the same as those in Example 1 except that the obtained sample was calcined in a muffle furnace at 200° C.

Example 23

The procedures were the same as those in Example 1 except that the obtained sample was calcined in a muffle furnace at 600° C.

Example 24

The procedures were the same as those in Example 1 except that the obtained sample was calcined in a muffle furnace for 1h.

Example 25

The procedures were the same as those in Example 1 except that the obtained sample was calcined in a muffle furnace for 20h.

Example 26

Figure 1:
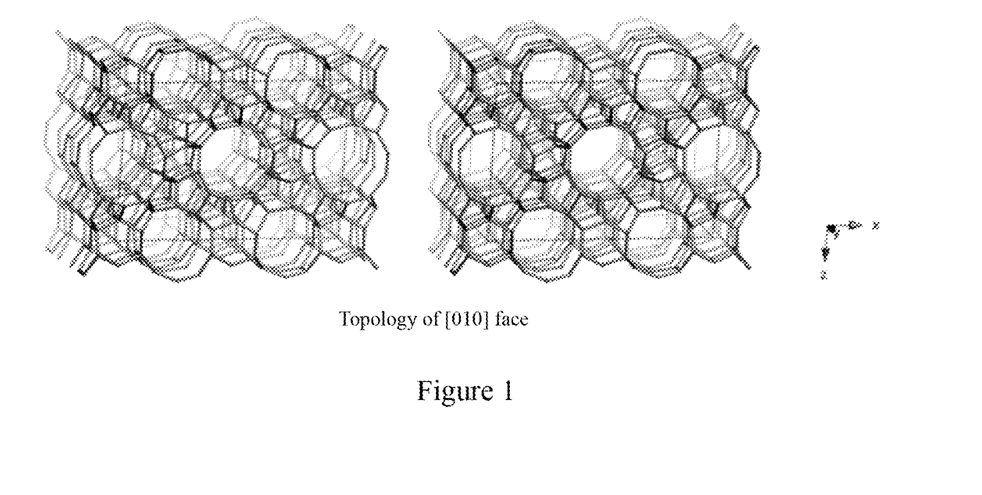
FIG. 1 shows the topology of TNU-9 molecular sieve.
Figure 2:
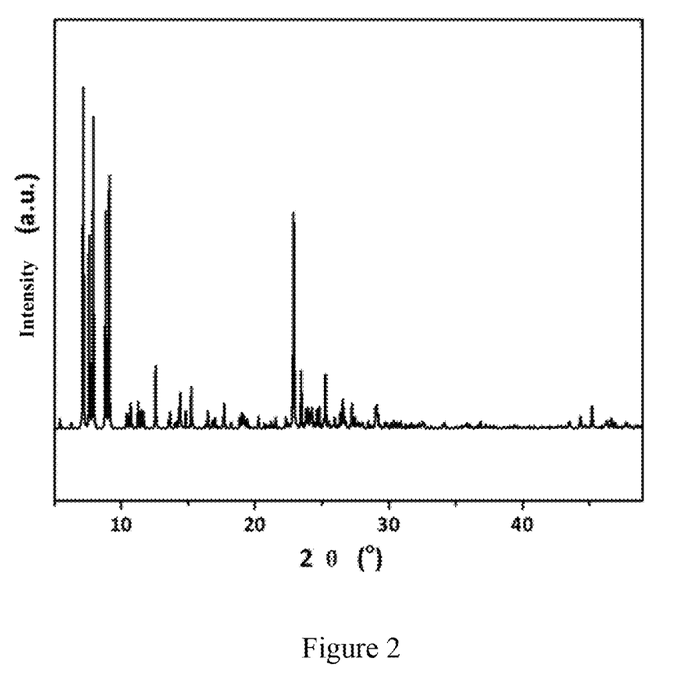
FIG. 2 shows the XRD pattern of the TNU-9 catalyst in Example 1 before the catalytic reaction.

The TNU-9 molecular sieves obtained in Examples 1 to 25 were subject to XRD characterization. A typical XRD pattern is shown in FIG. 2, and corresponds to the TNU-9 molecular sieve in Example 1. XRD pattern shows that the synthesized molecular sieve is TNU-9 molecular sieve. In the XRD pattern, the diffraction peak intensities at 2θ=7.142°, 7.588°, 7.887°, 8.819°, 9.080°, 12.556°, 14.395°, 15.215°, 22.878°, 22.908°, 23.444°, 25.263° are relatively strong, and the three strongest peak appear at 2θ=7.142°, 7.887° and 9.080°.

The XRD patterns of other samples are similar to those in FIG. 2, and show that TNU-9 molecular sieves have been successfully prepared.

Example 27

Figure 4:
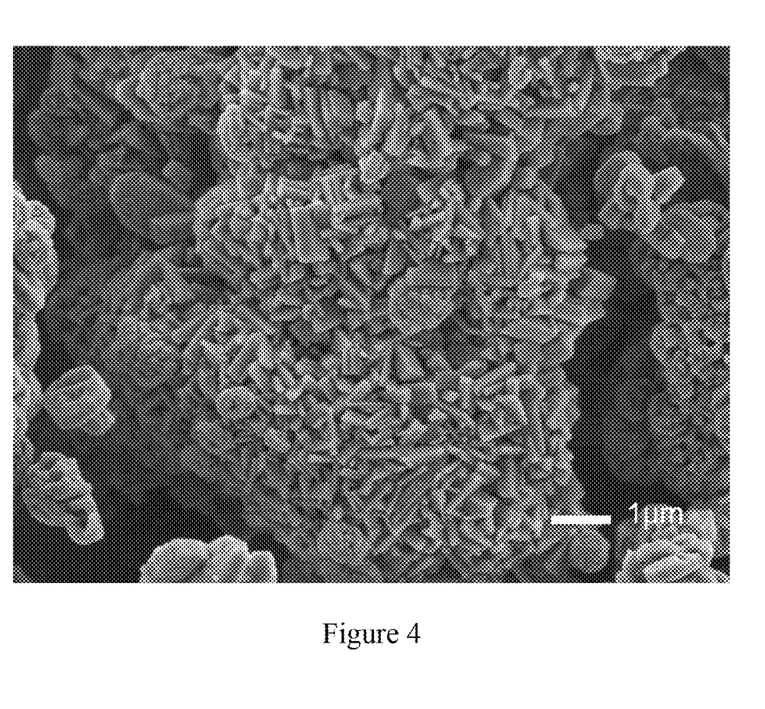
FIG. 4 shows the SEM image of the TNU-9 catalyst in Example 1 before the catalytic reaction.

The TNU-9 molecular sieves obtained in Examples 1 to 25 were subject to SEM characterization. A typical SEM image is shown in FIG. 4, and corresponds to the TNU-9 molecular sieve in Example 1. The SEM image shows that the molecular sieve is in the form of a small crystal grain accumulation, the diameter of a single crystal grain ranges from 100 to 1000 nm, and the small crystal grains have an irregular morphology, or a flaky structure with a thickness of about 20 nm.

Figure 3:
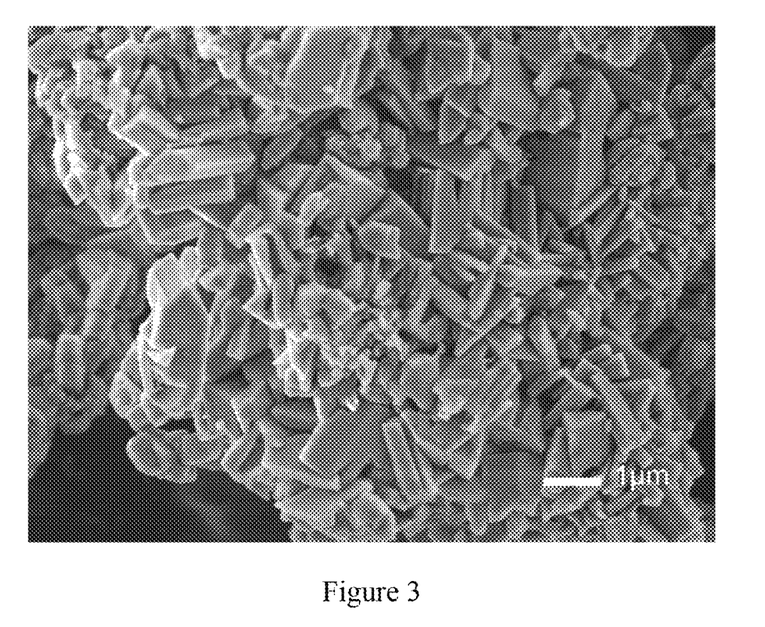
FIG. 3 shows the SEM image of the TNU-9 catalyst in Example 1 before the catalytic reaction.

The SEM images of other samples are similar to FIGS. 3 and 4, and the morphology is in the form of the small crystal grain or flake-like crystal grain accumulation, and the diameter of a single crystal grain ranges from 100 to 1000 nm.

Example 28

Figure 5:
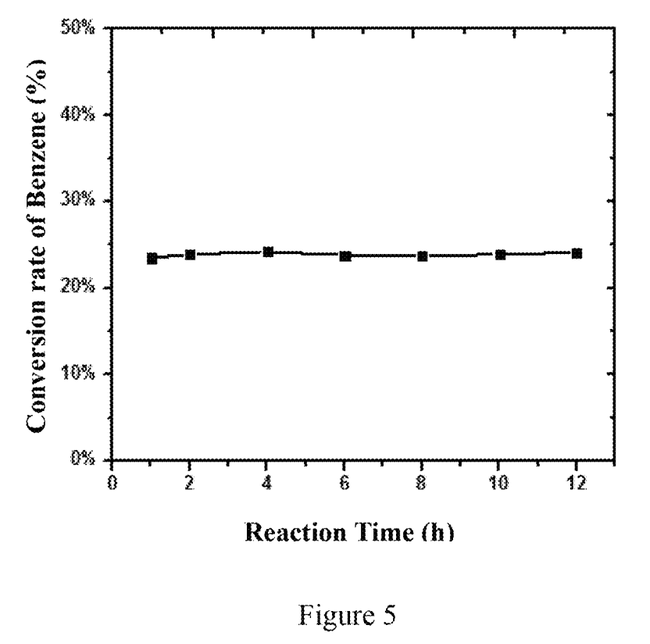
FIG. 5 shows the conversion rate of benzene in the vapor-phase alkylation reaction of ethanol and benzene by using the catalyst in Example 1 to produce ethylbenzene.
Figure 6:
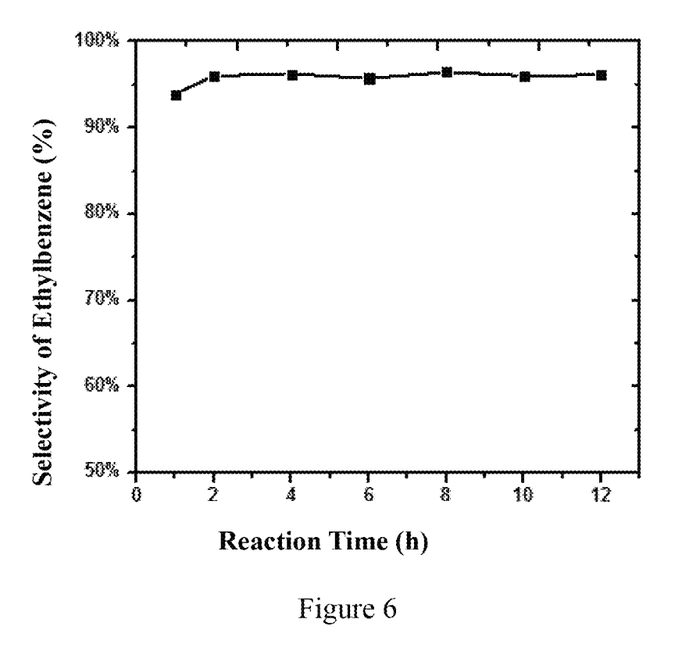
FIG. 6 shows the selectivity of ethylbenzene in the production of ethylbenzene from ethanol by using the catalyst in Example 1.

The catalyst in Example 1 was loaded in the reaction tube of the fixed bed reaction bed for evaluating catalytic performance of the catalyst. The raw materials were benzene and ethanol, and the molar ratio of benzene to ethanol was 4:1, the reaction temperature was 390° C., the weight hourly space velocity is 5.5 $h^{-1}$, and the reaction pressure is atmospheric pressure. The catalytic performance is shown in FIGS. 5 and 6. FIG. 5 shows that within the reaction time in a range from 0 to 12 h, the conversion rate of benzene is above 22%, and the conversion rate remains basically unchanged. FIG. 6 shows that within the reaction time in a range from 0 to 12 h, the selectivity of ethylbenzene is above 92%, and the selectivity remains basically unchanged. FIGS. 5 and 6 show that the catalyst has good stability and excellent catalytic performance, and achieves high conversion rate of the reactant and high selectivity of the target product.

The catalytic performances achieved by the catalysts in other examples are similar to those in FIGS. 5 and 6.

Example 29

The catalysts in Examples 1 to 25 were loaded in the reaction tube of a fixed bed reaction bed for evaluating catalytic performance of the catalyst. The raw materials were benzene and ethanol, and the molar ratio of benzene to ethanol was 6:1, the reaction temperature was 390° C., the weight hourly space velocity was 6.5 $h^{-1}$, and the reaction pressure was atmospheric pressure. The catalytic results of the catalysts in Examples 1 to 16 are shown in table 1. Table 1 shows that the molecular sieve catalysts prepared in Examples 1 to 16 of the present application achieves the following results in the vapor-phase alkylation reaction of ethanol and benzene: the conversion rate of ethanol is above 99%, the conversion rate of benzene is above 15%, and the selectivity of ethylbenzene is above 98%. Compared with Comparative Example 1 and Comparative Example 2, the TNU-9 molecular sieve catalyst prepared in the present application achieves nearly identical catalytic activity to that Comparative Example 1 and Comparative Example 2 achieve. In addition, it can be seen from table 1 that, where the TNU-9 molecular sieve catalyst prepared in this application is used to catalyze the vapor-phase alkylation reaction of ethanol and benzene, the content of the xylene as by-product is as low as 540 ppm. In contrast, where the molecular sieve catalysts in comparative Examples 1 and 2 are used to catalyze the vapor-phase alkylation reaction of ethanol and benzene, the content of the xylene as by-product is above 850 ppm. Thus, the product produced by using the catalyst in the present application has higher purity.

The reaction results of Examples 17 to 25 are similar to Example 1.

Comparative Example 1

The catalyst in the comparative example 1 used the nano ZSM-5 molecular sieve catalyst ($SiO_2/Al_2O_3$=25) which was purchased from Nankai Molecular Sieve Factory, and the conditions for evaluating the catalytic performance of the catalyst were the same as those in Example 28. The results of the catalytic reaction are shown in Table 1.

Comparative Example 2

The catalyst in the comparative example 2 used the nano ZSM-5 molecular sieve catalyst ($SiO_2/Al_2O_3$=25) purchased from Nankai Molecular Sieve Factory, and the conditions for evaluating the catalytic performance of the catalyst were the same as those in Example 28. The results of the catalytic reaction are shown in Table 1.

TABLE 1

Catalytic performance of the catalysts used in the vapor-phase alkylation reaction of ethanol and benzene

| Catalyst | Conversion rate of Ethanol/% | Conversion rate of Benzene/% | Selectivity of Ethylbenzene/% | Xylene content/ ppm |
|---|---|---|---|---|
| Example 1 | 99.8 | 16.7 | 99.8 | 540 |
| Example 2 | 99.5 | 16.4 | 99.6 | 560 |
| Example 3 | 99.3 | 16.2 | 99.4 | 590 |
| Example 4 | 99.6 | 16.5 | 99.6 | 620 |
| Example 5 | 99.1 | 15.8 | 98.7 | 780 |
| Example 6 | 98.7 | 15.4 | 98.6 | 850 |
| Example 7 | 99.5 | 16.2 | 99.3 | 680 |
| Example 8 | 99.3 | 16.3 | 99.5 | 620 |
| Example 9 | 99.7 | 16.5 | 99.7 | 640 |
| Example 10 | 99.2 | 16.0 | 99.0 | 750 |
| Example 11 | 98.1 | 15.6 | 98.2 | 890 |
| Example 12 | 98.6 | 15.4 | 98.0 | 870 |
| Example 13 | 97.6 | 15.1 | 97.6 | 930 |
| Example 14 | 99.4 | 16.1 | 99.2 | 680 |
| Example 15 | 99.6 | 16.3 | 99.3 | 620 |
| Example 16 | 99.5 | 16.3 | 99.5 | 640 |
| Comparative Example 1 | 99.6 | 24.6 | 99.4 | 1100 |
| Comparative Example 2 | 99.8 | 16.6 | 99.8 | 850 |

Note:
Xylene content is the content of xylene relative to ethylbenzene in the product.

Example 30

The TNU-9 molecular sieve catalysts obtained in Examples 1 to 25, the nano ZSM-5 molecular sieve catalysts in Comparative Examples 1 and 2 were tested in terms of hydrothermal stability.

The catalysts were respectively calcined at 650° C. for 4 h, and the relative crystallinity of the calcined catalysts was measured. Experimental results show that the relative crystallinity of the TNU-9 molecular sieve catalysts obtained in Examples 1 to 25 decreased by about 15%, and the relative crystallinity of the nano ZSM-5 molecular sieve catalysts in Comparative Examples 1 and 2 decreased by about 16%.

The catalysts were respectively treated with saturated water steam at 800° C. for 8 hours, and then the relative crystallinity of the catalysts was measured. The experimental results show that the relative crystallinity of the TNU-9 molecular sieve catalysts obtained in Examples 1 to 25 decreased by about 30%, and the relative crystallinity of the nano ZSM-5 molecular sieve catalysts in Comparative Examples 1 and 2 decreased by about 28%.

The thermal stability and hydrothermal stability of the catalysts in Examples 1 to 25 and in Comparative Examples 1 and 2 are similar.

Though the present application has been described above with reference to preferred examples, these examples are not intended to limit the present application. Without departing from the spirit of the present application, the skilled in the art will be able to make several possible variations or modifications, which are equivalent examples and fall within the protection scope of the technical solutions of the present application.

The invention claimed is:
1. A method for producing ethylbenzene by vapor-phase alkylation of ethanol and benzene comprising the following steps:
feeding raw materials comprising benzene and ethanol to a fixed bed reactor loaded with a molecular sieve catalyst to react to obtain ethylbenzene;

wherein the molecular sieve catalyst is mesoporous-microporous composite TNU-9 molecular sieve, wherein a silica to alumina molar ratio, $SiO_2/Al_2O_3$, of the mesoporous-microporous composite TNU-9 molecular sieve ranges from 50 to 200; wherein the mesoporous-microporous composite TNU-9 molecular sieve comprises a mesopore channel, a diameter of which ranges from 3 to 50 nm; a reaction temperature ranges from 300 to 500° C., a reaction pressure ranges from 0.1 to 2 MPa, a molar ratio of benzene to ethanol in the raw materials ranges from 3:1 to 7:1, and a weight hourly space velocity of the raw materials ranges from 3 to 8 $h^{-1}$.

2. The method for producing ethylbenzene by vapor-phase alkylation of ethanol and benzene according to claim 1, wherein the silica to alumina molar ratio, $SiO_2/Al_2O_3$, of the mesoporous-microporous composite TNU-9 molecular sieve ranges from 50 to 100.

3. The method for producing ethylbenzene by vapor-phase alkylation of ethanol and benzene according to claim 1, wherein the silica to alumina molar ratio, $SiO_2/Al_2O_3$, of the mesoporous-microporous composite TNU-9 molecular sieve ranges from 60 to 100.

4. The method for producing ethylbenzene by vapor-phase alkylation of ethanol and benzene according to claim 1, wherein the silica to alumina molar ratio, $SiO_2/Al_2O_3$, of the mesoporous-microporous composite TNU-9 molecular sieve ranges from 60 to 80.

5. The method for producing ethylbenzene by vapor-phase alkylation of ethanol and benzene according to claim 1, wherein the mesoporous-microporous composite TNU-9 molecular sieve is in a form of crystal grain accumulation, and a diameter of a single crystal grain ranges from 100 to 1000 nm.

6. The method for producing ethylbenzene by vapor-phase alkylation of ethanol and benzene according to claim 1, wherein a preparation method for the molecular sieve catalyst comprises the following steps:
    (1) adding an aluminum source, an alkali source, and a silicon source comprising mesopore structure to an aqueous solution containing a template and then stirring to obtain a gel-like precursor;
    (2) crystallizing hydrothermally the gel-like precursor obtained in step (1);
    (3) washing a product obtained in step (2) to be neutral and drying the product; and
    (4) calcining the product obtained in step (3) to obtain the molecular sieve catalyst.

7. The method for producing ethylbenzene by vapor-phase alkylation of ethanol and benzene according to claim 6, wherein a molar ratio of the aluminum source, alkali source, silicon source comprising mesopore structure, and template in step (1) satisfies: $SiO_2:Al_2O_3:M_2O:R:H_2O=$ (5~100):1:(1~30):(5~20):(1000~4000);
    wherein, R represents the template and is calculated by a molar number of the template itself, a molar number of the aluminum source is calculated by a molar number of $Al_2O_3$, a molar number of the alkali source is calculated by a molar number of its corresponding alkali metal oxide $M_2O$, a molar number of the silicon source is calculated by a molar number of $SiO_2$, and a molar number of water is calculated by a molar number of $H_2O$ itself;
    the template in step (1) comprises at least one of 1,4-MPB, glucose and activated carbon.

8. The method for producing ethylbenzene by vapor-phase alkylation of ethanol and benzene according to claim 7, wherein a method for preparing 1,4-MPB comprises: subjecting a solution comprising 1,4-dibromobutane and N-methyltetrahydropyrrole to refluxing, recrystallizing and drying to obtain 1,4-MPB.

9. The method for producing ethylbenzene by vapor-phase alkylation of ethanol and benzene according to claim 8, wherein the solution comprising 1,4-dibromobutane and N-methyltetrahydropyrrole is obtained by placing 1,4-dibromobutane and N-methyltetrahydropyrrole in acetone;
    the refluxing is performed at a temperature ranging from 30 to 80° C. in water bath, and a time for the refluxing in water bath ranges from 6 to 48 h;
    a step of extraction by acetone occurs before the recrystallization;
    a solvent for recrystallization includes a mixed solvent of methanol and diethyl ether, wherein a volume ratio of methanol and diethyl ether is (0.05~50):(1~20);
    the drying is performed at a temperature ranging from 60 to 120° C. for a time ranging from 5 to 20 h.

10. The method for producing ethylbenzene by vapor-phase alkylation of ethanol and benzene according to claim 6, wherein the silicon source comprising mesopore structure in step (1) is at least one of silica comprising mesopore structure, MCM-48, and SBA-15.

11. The method for producing ethylbenzene by vapor-phase alkylation of ethanol and benzene according to claim 6, wherein the aluminum source in step (1) is at least one of sodium metaaluminate, aluminum powder, aluminum nitrate and aluminum hydroxide;
    the alkali source is at least one of sodium hydroxide and potassium hydroxide.

12. The method for producing ethylbenzene by vapor-phase alkylation of ethanol and benzene according to claim 6, wherein a time for stirring in step (1) ranges from 5 to 24 h.

13. The method for producing ethylbenzene by vapor-phase alkylation of ethanol and benzene according to claim 6, wherein a hydrothermal crystallization in step (2) is hydrothermal dynamic crystallization, and the hydrothermal dynamic crystallization is performed at a temperature ranging from 120 to 260° C. for a time ranging from 100 to 360 h.

14. The method for producing ethylbenzene by vapor-phase alkylation of ethanol and benzene according to claim 13, wherein the dynamic crystallization in step (2) is rotational crystallization, and the rotation speed ranges from 5 to 30 rpm.

15. The method for producing ethylbenzene by vapor-phase alkylation of ethanol and benzene according to claim 6, wherein step (3) comprises filtering and washing a product obtained in step (2) until a washing liquid is neutral, and then drying the product at a temperature ranging from 60 to 110° C.

16. The method for producing ethylbenzene by vapor-phase alkylation of ethanol and benzene according to claim 6, wherein a temperature for calcining in step (4) ranges from 200 to 600° C., and the time for calcining ranges from 1 to 20 h.

17. The method for producing ethylbenzene by vapor-phase alkylation of ethanol and benzene according to claim 6, wherein the preparation method for the molecular sieve catalyst comprises the following steps:
    1) synthesis of 1,4-MPB template R
        dissolving 1,4-dibromobutane and N-methyltetrahydropyrrole in acetone, heating them to a temperature ranging from 30 to 80° C., refluxing for a time ranging from 6 to 48 h; extracting a reaction solution obtained by acetone, and recrystallizing the obtained product by a mixed solvent of methanol and diethyl ether, drying the recrystallized product in a vacuum drying oven at a temperature ranging from 60 to 120° C. for a time ranging from 5 to 20 h to obtain the template R;

2) preparation of TNU-9 molecular sieve dissolving the template R obtained in step 1) in water, and then adding sequentially an aluminum source, an alkali source and a silicon source comprising mesopore structure to obtain a solution I, wherein a molar ratio of raw materials in the solution I was $SiO2:Al_2O_3:M_2O:R:H2O=(5\sim100):1:(1\sim30):(5\sim20):(1000\sim4000)$; after stirring for a time ranging from 5 to 24h, the solution I will form a gel; putting the gel into a reactor, and performing crystallization for a time ranging from 100 to 360h under the dynamic and hydrothermal conditions driven by a motor at a temperature ranging from 120 to 260° C.; filtering and washing the obtained product until a washing liquid is neutral, and drying a filter cake at a temperature ranging from 60 to 110° C.; calcining the dried filter cake in a muffle furnace at a temperature ranging from 200 to 600° C. for a time ranging from 1 to 20 h to obtain the molecular sieve catalyst.

\* \* \* \* \*